United States Patent
Chow et al.

(10) Patent No.: US 6,669,831 B2
(45) Date of Patent: Dec. 30, 2003

(54) MICROFLUIDIC DEVICES AND METHODS TO REGULATE HYDRODYNAMIC AND ELECTRICAL RESISTANCE UTILIZING BULK VISCOSITY ENHANCERS

(75) Inventors: Andrea W. Chow, Los Altos, CA (US); Carlton Brooks, Menlo Park, CA (US)

(73) Assignee: Caliper Technologies Corp., Mountain View, CA (US)

( * ) Notice: Subject to any disclaimer, the term of this patent is extended or adjusted under 35 U.S.C. 154(b) by 125 days.

(21) Appl. No.: 09/854,141

(22) Filed: May 10, 2001

(65) Prior Publication Data

US 2002/0046948 A1 Apr. 25, 2002

Related U.S. Application Data

(60) Provisional application No. 60/203,498, filed on May 11, 2000.

(51) Int. Cl.$^7$ .......................... B01D 57/02; G01N 21/76
(52) U.S. Cl. .................. 204/450; 204/600; 137/804; 436/174; 436/179; 422/99; 422/102
(58) Field of Search ................. 204/450, 600; 137/804; 436/174, 179; 422/99, 102

(56) References Cited

U.S. PATENT DOCUMENTS

| | | |
|---|---|---|
| 4,390,403 A | 6/1983 | Batchelder |
| 4,908,112 A | 3/1990 | Pace |

(List continued on next page.)

FOREIGN PATENT DOCUMENTS

| | | |
|---|---|---|
| WO | WO 96/04547 | 2/1996 |
| WO | WO 97/02357 | 1/1997 |
| WO | WO 98/00231 | 1/1998 |
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/56954 | 11/1999 |
| WO | WO 00/09753 | 2/2000 |
| WO | WO 01/14064 | 3/2001 |

OTHER PUBLICATIONS

Cohen, C.B. et al., "A Microchip–Based Enzyme Assay for Protein Kinase A," Anal. Chem. (1999) 273:89–97, no month.

(List continued on next page.)

Primary Examiner—Arun S. Phasge
(74) Attorney, Agent, or Firm—Donald R. McKenna; Quine Intellectual Property Law Group

(57) ABSTRACT

Methods and devices for inducing high bulk hydrodynamic resistance and/or for inducing low electrical resistance in microscale systems including bulk viscosity enhancers, surfactants, and electrolytes. High bulk hydrodynamic resistance is optionally utilized to regulate the effects of spontaneous injection and/or dispersion. Induced high hydrodynamic resistance in conjunction with induced low electrical resistance are optionally utilized to provide and regulate electrical fields within microfluidic devices. Integrated systems incorporating the methods of the invention are also provided.

46 Claims, 6 Drawing Sheets

U.S. PATENT DOCUMENTS

| | | |
|---|---|---|
| 5,126,022 A | 6/1992 | Soane et al. |
| 5,498,392 A | 3/1996 | Wilding et al. |
| 5,571,410 A | 11/1996 | Swedberg et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,603,351 A | 2/1997 | Cherukuri et al. |
| 5,635,358 A | 6/1997 | Wilding et al. |
| 5,637,469 A | 6/1997 | Wilding et al. |
| 5,699,157 A | 12/1997 | Parce |
| 5,750,015 A | 5/1998 | Soane et al. |
| 5,779,868 A | 7/1998 | Parce et al. |
| 5,800,690 A | 9/1998 | Chow et al. |
| 5,842,787 A | 12/1998 | Kopf-Sill et al. |
| 5,852,495 A | 12/1998 | Parce |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,885,470 A * | 3/1999 | Parce et al. .................... 216/33 |
| 5,942,443 A | 8/1999 | Parce et al. |
| 5,948,227 A | 9/1999 | Dubrow |
| 5,955,028 A | 9/1999 | Chow |
| 5,957,579 A | 9/1999 | Kopf-Sill et al. |
| 5,958,203 A | 9/1999 | Parce et al. |
| 5,958,694 A | 9/1999 | Nikiforov |
| 5,959,291 A | 9/1999 | Jensen |
| 5,964,995 A | 10/1999 | Nikiforov et al. |
| 5,965,001 A | 10/1999 | Chow et al. |
| 5,965,410 A | 10/1999 | Chow et al. |
| 5,972,187 A | 10/1999 | Parce et al. |
| 5,976,336 A | 11/1999 | Dubrow et al. |
| 5,989,402 A | 11/1999 | Chow et al. |
| 6,001,231 A | 12/1999 | Kopf-Sill |
| 6,004,515 A | 12/1999 | Parce et al. |
| 6,011,252 A | 1/2000 | Jensen |
| 6,012,902 A | 1/2000 | Parce |
| 6,042,710 A | 3/2000 | Dubrow |
| 6,046,056 A | 4/2000 | Parce et al. |
| 6,068,752 A | 5/2000 | Dubrow et al. |
| 6,071,478 A | 6/2000 | Chow |
| 6,074,725 A | 6/2000 | Kennedy |
| 6,080,295 A | 6/2000 | Parce et al. |
| 6,156,181 A | 12/2000 | Parce et al. |
| 6,444,461 B1 * | 9/2002 | Knapp et al. ............. 435/283.1 |

OTHER PUBLICATIONS

Dasgupta, P.K. et al., "Electroosmosis: A Reliable Fluid Propulsion System for Flow Injection Analysis," *Anal. Chem.* (1994) 66:1792–1798, no month.

Jacobson, S.C. et al., "Fused Quartz Substrates for Microchip Electrophoresis," *Anal. Chem.* (1995) 67:2059–2063, no month.

Manz, A. et al., "Electrosmotic pumping and electrophoretic separations for miniaturized chemical analysis systems," *J. Micromech. Microeng.* (1994) 4:257–265.

Ramsey, J.M. et al., "Microfabricated chemical measurement systems," *Nature Med.* (1995) 1:1093–1096, no month.

Seiler, K. et al., "Planar Glass Chips for Capillary Electrophoresis: Repetitve Sample Injection, Quantitation, and Separation Efficiency," *Anal. Chem.* (1993) 65:1481–1488

Seiler, K. et al., "Electroosmotic Pumping and Valveless Control of Fluid Flow Within a Manifold of Capillaries on a Glass Chip," *Anal. Chem.* (1994) 66:3485–3491, no month.

Sundberg, S. A., "High-throughput and ultra-high-throughput screening: solution—and cell—based approches," *Current Opinions in Biotechnology* 2000, 11:47–53, no month.

* cited by examiner

MICROFLUIDIC DEVICES AND METHODS TO REGULATE HYDRODYNAMIC AND ELECTRICAL RESISTANCE UTILIZING BULK VISCOSITY ENHANCERS

CROSS-REFERENCES TO RELATED APPLICATIONS

Pursuant to 35 U.S.C. §§ 119 and/or 120, and any other applicable statute or rule, this application claims the benefit of and priority to U.S. Ser. No. 60/203,498, filed on May 11, 2000, the disclosure of which is incorporated by reference.

COPYRIGHT NOTIFICATION

Persuant to 37 C.F.R. § 1.71(e), Applicant note that a portion of this disclosure contains material which is subject to copyright protection. The coptright owner has no objection to the facsimile reproduction by anyone of the present document or patent disclosure, as it appears in the Patent and Trademark Office patent file or records, but otherwise reserves all copyright rights whatsoever.

BACKGROUND OF THE INVENTION

Microfluidic devices generally provide reliable, accurate and high-throughput methods of performing diverse instrumental analyses, including various screening protocols and separation-based assays. Additionally, many microfluidic devices have been inexpensively incorporated as components of automated systems. Despite these attributes, certain limitations or inefficiencies exist, which, if overcome, would further enhance the utility of these devices and systems.

To illustrate, the phenomenon of spontaneous injection, while useful in certain microfluidic applications, can also be a limiting factor in others. It is typically caused by the surface tension present in a drop of fluid suspended from a capillary microchannel in certain devices. The surface tension tends to produce an inward pressure that forces (i.e., spontaneously injects) fluid into the capillary microchannel. Pressure variations due to spontaneous injection can generate flow rate fluctuations in a microfluidic device which can give rise to periodic fluctuations in the baseline signal of an associated detector. In turn, these baseline signal fluctuations can obscure detectable signals produced by assay components.

One method used to control the effects of spontaneous injection has been to alter certain geometric parameters, such as the diameter of a capillary microchannel. Another approach has been to maintain a relatively high dilution factor in such a microchannel. Both methods have also been used simultaneously. Additionally, temperature has been used to vary buffer viscosity in capillary microchannels. This approach can adversely impact the rates of certain biochemical assays.

Some microfluidic applications utilize microchannels simultaneously having both high hydrodynamic resistance and low electrical resistance, e.g., to deliver electrical fields to a reaction microchannel. Since hydrodynamic and electrical resistances have different design parameters related to channel depth, one technique for achieving these conditions has been to manufacture side microchannels shallower and wider than the reaction microchannel. However, microfluidic devices which include multiple microchannel depths can be more costly and difficult to fabricate than comparable single depth devices.

Accordingly, it would be advantageous to provide additional techniques for overcoming these limitations and inefficiencies, especially techniques for tailoring various characteristics of microfluidic devices during operation. The present invention provides additional methods and devices for controlling the effects of spontaneous injection and for regulating electric fields within microfluidic devices and systems.

SUMMARY OF THE INVENTION

The present invention provides methods and devices for inducing high bulk hydrodynamic resistance in microfluidic devices, e.g., to minimize the spontaneous injection signatures of the devices. The invention also relates to methods and devices for inducing low electrical resistance, in addition to high hydrodynamic resistance, in microfluidic devices, inter alia, for regulating electrical resistance within the devices.

The methods of inducing high bulk hydrodynamic resistance include providing a microscale cavity (e.g., a capillary microchannel) in the microfluidic device that includes a bulk viscosity enhancer disposed in the cavity. The microscale cavity optionally also includes a capillary microchannel that extends from the microfluidic device. The bulk viscosity enhancer effects an increase in bulk hydrodynamic resistance within the microscale cavity of the microfluidic device. Additionally, the bulk viscosity enhancer is, e.g., a polymer molecule that has a molecular weight of at least about one kilodalton. For example, bulk viscosity enhancers typically have molecular weights in the range of from about one kilodalton to about 1,000 kilodaltons, generally in the range of from about 5 kilodaltons to about 100 kilodaltons, e.g., about 50 kilodaltons. Suitable bulk viscosity enhancers include biocompatible polymers. For example, bulk viscosity enhancers optionally include one or more of: a single polymer, a mixture of polymers, a copolymer, a block copolymer, a polymer micellar system, an interpenetrating polymer network, a polymer gel, a polysaccharide (e.g., FICOLL™, dextran, etc.), poly(ethylene glycol) (PEG), poly(vinyl alcohol) (PVA), poly(dimethylacryamide) (PDMA), derivatives thereof, or the like. Bulk viscosity enhancers are typically disposed in aqueous solutions.

Bulk hydrodynamic resistance in the microscale cavity in the device is regulated, e.g., by varying or selecting a concentration of the bulk viscosity enhancer disposed in the cavity, by varying or selecting a temperature within the microscale cavity, or both. The regulated bulk hydrodynamic resistance regulates spontaneous injection into the microscale cavity, e.g., during operation of the microfluidic device. Spontaneous injection is also optionally regulated by varying or selecting a concentration of a surfactant disposed in the microscale cavity. In another aspect of the invention, the regulated bulk hydrodynamic resistance regulates dispersion (e.g., slug dispersion) during fluid flow in the microscale cavity.

The methods of inducing high bulk hydrodynamic resistance optionally further include inducing low electrical resistance in the microfluidic device. The methods include, e.g., providing an electrolyte (e.g., a salt, a buffering ionic species, etc.) disposed in the microscale cavity (e.g., a microchannel). The diffusive mobility of the electrolyte is substantially unaffected by the increase in bulk hydrodynamic resistance within the microscale cavity, e.g., due to the small size of the electrolyte relative to the hydrodynamic radius of the bulk viscosity enhancer. As a result, low electrical resistance is induced in the microfluidic device. Furthermore, both the bulk viscosity enhancer and the electrolyte are optionally flowed in the microfluidic device using a fluid direction component that includes, e.g., a fluid pressure force modulator, an electrokinetic force modulator, a capillary force modulator, a fluid wicking element, or the like.

Bulk hydrodynamic resistance and electrical resistance in the microscale cavity in the microfluidic device are optionally individually or concomitantly regulated by varying or selecting a concentration of the at least one bulk viscosity enhancer and/or a concentration of the at least one electrolyte disposed in the cavity. Optionally, the bulk hydrodynamic resistance, the electrical resistance, or both, in the microscale cavity are regulated, e.g., during operation of the microfluidic device. Additionally, the methods optionally include providing a microchannel disposed in the microfluidic device that intersects and fluidly communicates with the microscale cavity. Regulating the electrical resistance in the at least one microscale cavity regulates electrical resistance in the at least one microchannel. Furthermore, the bulk viscosity enhancer and/or the electrolyte are optionally chosen to modify the electroosmotic velocity in the at least one microscale cavity.

The present invention also includes a device or system that includes a body structure that includes a microscale cavity (e.g., a capillary microchannel) extending from the body structure. The microscale cavity also includes a bulk viscosity enhancer disposed in the cavity. As mentioned, the bulk viscosity enhancer includes, e.g., a polymer molecule that includes a molecular weight of at least about one kilodalton. For example, bulk viscosity enhancers typically have molecular weights in the range of from about one kilodalton to about 1,000 kilodaltons, generally in the range of from about 5 kilodaltons to about 100 kilodaltons, e.g., about 50 kilodaltons. Additionally, preferred bulk viscosity enhancers include biocompatible polymers. Suitable bulk viscosity enhancers generally include one or more of: a single polymer, a mixture of polymers, a copolymer, a block copolymer, a polymer micellar system, an interpenetrating polymer network, a polymer gel, a polysaccharide, PEG, PVA, PDMA, derivatives thereof, or the like. Furthermore, bulk viscosity enhancers are typically disposed in aqueous solutions.

The device or system optionally further includes an integrated system that includes a computer or a computer readable medium that includes an instruction set for varying or selecting a concentration of the bulk viscosity enhancer disposed in the microscale cavity, for varying or selecting a temperature within the microscale cavity, or both. The microscale cavity optionally includes a capillary microchannel that extends from the microfluidic device. The varied or selected bulk viscosity enhancer concentration regulates bulk hydrodynamic resistance within the microscale cavity which, in turn, regulates spontaneous injection into the microscale cavity, e.g., during operation of the device. Optionally, the device or system also includes regulating spontaneous injection by varying or selecting a concentration of a surfactant disposed in the microscale cavity. In another aspect, the regulated bulk hydrodynamic resistance within the microscale cavity regulates dispersion (e.g., slug dispersion) during fluid flow in the microscale cavity.

The invention also includes a device or system that includes a body structure having a microscale cavity (e.g., a microchannel) fabricated in the structure in which the microscale cavity optionally includes a mixture of a bulk viscosity enhancer and an electrolyte (e.g., a salt, a buffering ionic species, or the like) disposed in the cavity. This device or system also optionally includes an integrated system that includes a computer or a computer readable medium that includes an instruction set. The instruction set varies or selects concentrations of the bulk viscosity enhancer and the electrolyte disposed in the microscale cavity to regulate bulk hydrodynamic resistance and electrical resistance within the microscale cavity.

The device also optionally includes a microchannel fabricated in the body structure. The microchannel intersects and fluidly communicates with the microscale cavity (which, in turn optionally comprises a microchannel) in which case, regulating the electrical resistance within the microscale cavity regulates electrical resistance in the microchannel. Furthermore, the bulk hydrodynamic resistance, the electrical resistance, or both, are optionally regulated within the microscale cavity during operation of the device.

The present invention also typically includes flowing the bulk viscosity enhancer and/or the electrolyte in the device or system using a fluid direction component that includes a fluid pressure force modulator, an electrokinetic force modulator, a capillary force modulator, a fluid wicking element, or the like.

DETAILED DISCUSSION OF THE INVENTION

I. Introduction

Figure 1:
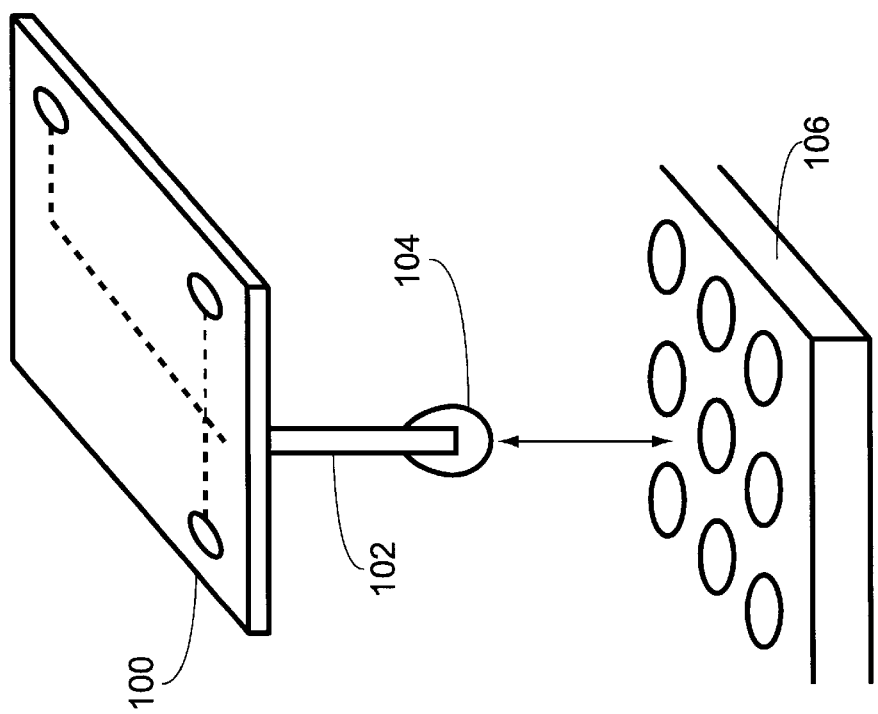
FIG. 1 schematically shows a microfluidic device that includes a capillary microchannel extending from the device for loading materials from the wells of a microtiter plate or similar storage device.

The present invention is generally directed to improved methods, and devices related thereto, for inducing high bulk hydrodynamic resistance and/or for inducing low electrical resistance in microfluidic devices and systems. High bulk hydrodynamic resistance is used, e.g., to control signal fluctuations caused by spontaneous injections into a device. Induced high hydrodynamic resistance used in conjunction with induced low electrical resistance provides significant advantages in the regulation of electrical fields and relative flow rate ratios of reagents and buffers within microfluidic devices. In particular, the methods include using bulk viscosity enhancers to modulate hydrodynamic resistance. An additional advantage of the present invention includes the capability of reconfiguring, or otherwise controlling, various microfluidic characteristics (e.g., spontaneous injection signatures, electrical fields, relative flow rates, or the like), not only during experimental design time, but also during operation of a microfluidic device. The phrase "during operation," as used herein, refers to the run time of a particular experiment or other application.

As used herein, the phrase "bulk hydrodynamic resistance" refers to the viscosity of a solution, which dictates convective motions. Further, bulk hydrodynamic resistance substantially affects only the diffusive mobility of larger components of a solution, such as molecules or other materials having molecular weights of at least about one kilodalton (e.g., proteins, polynucleotides, polymers, cells, and the like). The diffusive behavior of smaller components such as single atom ions, or other low molecular weight ions, is substantially unaffected by bulk hydrodynamic resistance. That is, aside from modified convective behaviors, smaller components generally diffuse relatively unimpeded through these solutions. For example, a solution optionally contains large polymer molecules (e.g., FICOLL™, dextran, agar, and the like) at concentrations that cause the solution to have high bulk hydrodynamic resistance (i.e., to be highly viscous). The same solution optionally also includes an electrolyte, such as KBr dissolved therein, in which $K^+$ and $Br^-$ ions migrate relatively freely through the solution by Brownian motions.

A variety of microscale systems are optionally adapted for use in the present invention, e.g., by incorporating bulk viscosity enhancers and/or electrolytes, as discussed below. These systems are described in various PCT applications and issued U.S. Patents by the inventors and their coworkers, including U.S. Pat. No. 5,699,157 (J. Wallace Parce) issued Dec. 16, 1997, U.S. Pat. No. 5,779,868 (J. Wallace Parce et al.) issued Jul. 14, 1998, U.S. Pat. No. 5,800,690 (Calvin Y. H. Chow et al.) issued Sep. 1, 1998, U.S. Pat. No. 5,842,787 (Anne R. Kopf-Sill et al.) issued Dec. 1, 1998, U.S. Pat. No. 5,852,495 (J. Wallace Parce) issued Dec. 22, 1998, U.S. Pat. No. 5,869,004 (J. Wallace Parce et al.) issued Feb. 9, 1999, U.S. Pat. No. 5,876,675 (Colin B. Kennedy) issued Mar. 2, 1999, U.S. Pat. No. 5,880,071 (J. Wallace Parce et al.) issued Mar. 9, 1999, U.S. Pat. No. 5,882,465 (Richard J. McReynolds) issued Mar. 16, 1999, U.S. Pat. No. 5,885,470 (J. Wallace Parce et al.) issued Mar. 23, 1999, U.S. Pat. No. 5,942,443 (J. Wallace Parce et al.) issued Aug. 24, 1999, U.S. Pat. No. 5,948,227 (Robert S. Dubrow) issued Sep. 7, 1999, U.S. Pat. No. 5,955,028 (Calvin Y. H. Chow) issued Sep. 21, 1999, U.S. Pat. No. 5,957,579 (Anne R. Kopf-Sill et al.) issued Sep. 28, 1999, U.S. Pat. No. 5,958,203 (J. Wallace Parce et al.) issued Sep. 28, 1999, U.S. Pat. No. 5,958,694 (Theo T. Nikiforov) issued Sep. 28, 1999, U.S. Pat. No. 5,959,291 (Morten J. Jensen) issued Sep. 28, 1999, U.S. Pat. No. 5,964,995 (Theo T. Nikiforov et al.) issued Oct. 12, 1999, U.S. Pat. No. 5,965,001 (Calvin Y. H. Chow et al.) issued Oct. 12, 1999, U.S. Pat. No. 5,965,410 (Calvin Y. H. Chow et al.) issued Oct. 12, 1999, U.S. Pat. No. 5,972,187 (J. Wallace Parce et al.) issued Oct. 26, 1999, U.S. Pat. No. 5,976,336 (Robert S. Dubrow et al.) issued Nov. 2, 1999, U.S. Pat. No. 5,989,402 (Calvin Y. H. Chow et al.) issued Nov. 23, 1999, U.S. Pat. No. 6,001,231 (Anne R. Kopf-Sill) issued Dec. 14, 1999, U.S. Pat. No. 6,011,252 (Morten J. Jensen) issued Jan. 4, 2000, U.S. Pat. No. 6,012,902 (J. Wallace Parce) issued Jan. 11, 2000, U.S. Pat. No. 6,042,709 (J. Wallace Parce et al.) issued Mar. 28, 2000, U.S. Pat. No. 6,042,710 (Robert S. Dubrow) issued Mar. 28, 2000, U.S. Pat. No. 6,046,056 (J. Wallace Parce et al.) issued Apr. 4, 2000, U.S. Pat. No. 6,048,498 (Colin B. Kennedy) issued Apr. 11, 2000, U.S. Pat. No. 6,068,752 (Robert S. Dubrow et al.) issued May 30, 2000, U.S. Pat. No. 6,071,478 (Calvin Y. H. Chow) issued Jun. 6, 2000, U.S. Pat. No. 6,074,725 (Colin B. Kennedy) issued Jun. 13, 2000, U.S. Pat. No. 6,080,295 (J. Wallace Parce et al.) issued Jun. 27, 2000, U.S. Pat. No. 6,086,740 (Colin B. Kennedy) issued Jul. 11, 2000, U.S. Pat. No. 6,086,825 (Steven A. Sundberg et al.) issued Jul. 11, 2000, U.S. Pat. No. 6,090,251 (Steven A. Sundberg et al.) issued Jul. 18, 2000, U.S. Pat. No. 6,100,541 (Robert Nagle et al.) issued Aug. 8, 2000, U.S. Pat. No. 6,107,044 (Theo T. Nikiforov) issued Aug. 22, 2000, U.S. Pat. No. 6,123,798 (Khushroo Gandhi et al.) issued Sep. 26, 2000, U.S. Pat. No. 6,129,826 (Theo T. Nikiforov et al.) issued Oct. 10, 2000, U.S. Pat. No. 6,132,685 (Joseph E. Kersco et al.) issued Oct. 17, 2000, U.S. Pat. No. 6,148,508 (Jeffrey A. Wolk) issued Nov. 21, 2000, U.S. Pat. No. 6,149,787 (Andrea W. Chow et al.) issued Nov. 21, 2000, U.S. Pat. No. 6,149,870 (J. Wallace Parce et al.) issued Nov. 21, 2000, U.S. Pat. No. 6,150,119 (Anne R. Kopf-Sill et al.) issued Nov. 21, 2000, U.S. Pat. No. 6,150,180 (J. Wallace Parce et al.) issued Nov. 21, 2000, U.S. Pat. No. 6,153,073 (Robert S. Dubrow et al.) issued Nov. 28, 2000, U.S. Pat. No. 6,156,181 (J. Wallace Parce et al.) issued Dec. 5, 2000, U.S. Pat. No. 6,167,910 (Calvin Y. H. Chow) issued Jan. 2, 2001, U.S. Pat. No. 6,171,067 (J. Wallace Parce) issued Jan. 9, 2001, U.S. Pat. No. 6,171,850 (Robert Nagle et al.) issued Jan. 9, 2001, U.S. Pat. No. 6,172,353 (Morten J. Jensen) issued Jan. 9, 2001, U.S. Pat. No. 6,174,675 (Calvin Y. H. Chow et al.) issued Jan. 16, 2001, U.S. Pat. No. 6,182,733 (Richard J. McReynolds) issued Feb. 6, 2001, U.S. Pat. No. 6,186,660 (Anne R. Kopf-Sill et al.) issued Feb. 13, 2001, and U.S. Pat. No. 6,221,226 (Anne R. Kopf-Sill et al.) issued Apr. 24, 2001; and published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548, WO 98/55852, WO 98/56505, WO 98/56956, WO 99/00649, WO 99/10735, WO 99/12016, WO 99/16162, WO 99/19056, WO 99/19516, WO 99/29497, WO 99/31495, WO 99/34205, WO 99/43432, WO 99/44217, WO 99/56954, WO 99/64836, WO 99/64840, WO 99/64848, WO 99/67639, WO 00/07026, WO 00/09753, WO 00/10015, WO 00/21666, WO 00/22424, WO 00/26657, WO 00/42212, WO 00/43766, WO 00/45172, WO 00/46594, WO 00/50172, WO 00/50642, WO 00/58719, WO 00/60108, WO 00/70080, WO 00/70353, WO 00/72016, WO 00/73799, WO 00/78454, WO 01/02850, WO 01/14865, and WO 01/17797.

The methods of the invention are generally performed within fluidic channels along which bulk viscosity enhancers, electrolytes, surfactants, and other reagents are disposed and/or flowed. In some cases, the channels are simply present in a capillary channel or tube, e.g., a glass, fused silica, quartz or plastic capillary. The capillary channel is fluidly coupled to a source of, e.g., the bulk viscosity enhancer, surfactant, electrolyte or other reagent, which is then flowed along the capillary channel. In particularly preferred aspects, the channel is integrated into the body structure of a microfluidic device. As used herein, the term "microfluidic" generally refers to one or more fluid passages, chambers or conduits which have at least one internal cross-sectional dimension, e.g., depth, width, length, diameter, etc., that is less than 500 μm, and typically between about 0.1 μm and about 500 μm.

In the devices of the present invention, the microscale channels or cavities preferably have at least one cross-sectional dimension between about 0.1 μm and 200 μm, more preferably between about 0.1 μm and 100 μm, and often between about 0.1 μm and 50 μm. Accordingly, the microfluidic devices or systems prepared in accordance with the present invention typically include at least one microscale channel (i.e., microchannel), usually at least two intersecting microscale channels, and often, three or more intersecting channels disposed within a single body structure. Channel intersections may exist in a number of formats, including cross intersections, "Y" or "T" intersections, or any number of other structures whereby two channels are in fluid communication.

The body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

In preferred aspects, the bottom portion of the device comprises a solid substrate that is substantially planar in structure, and which has at least one substantially flat upper surface. A variety of substrate materials are optionally employed as the bottom portion. Typically, because the devices are microfabricated, substrate materials will be selected based upon their compatibility with known microfabrication techniques, e.g., photolithography, wet chemical etching, laser ablation, air abrasion techniques, LIGA, reactive ion etching, injection molding, embossing, and other techniques. The substrate materials are also generally selected for their compatibility with the full range of conditions to which the microfluidic devices may be exposed, including extremes of pH, temperature, electrolyte concentration, and application of electric fields. Accordingly, in some preferred aspects, the substrate material may include materials normally associated with the semiconductor industry in which such microfabrication techniques are regularly employed, including, e.g., silica-based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. Such polymeric substrates are readily manufactured using available microfabrication techniques, as described above, or from microfabricated masters, using well-known molding techniques, such as injection molding, embossing or stamping, or by polymerizing the polymeric precursor material within the mold (see U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., to provide enhanced fluid direction, e.g., as described in U.S. Pat. No. 5,885,470 (J. Wallace Parce et al.) issued Mar. 23, 1999, and which is incorporated herein by reference in its entirety for all purposes.

The channels and/or cavities of the microfluidic devices are typically fabricated into the upper surface of the bottom substrate or portion of the device, as microscale grooves or indentations, using the above described microfabrication techniques. The top portion or substrate also comprises a first planar surface, and a second surface opposite the first planar surface. In the microfluidic devices prepared in accordance with certain aspects of the methods described herein, the top portion also includes a plurality of apertures, holes or ports disposed therethrough, e.g., from the first planar surface to the second surface opposite the first planar surface.

The first planar surface of the top substrate is then mated, e.g., placed into contact with, and bonded to the planar surface of the bottom substrate, covering and sealing the grooves and/or indentations in the surface of the bottom substrate, to form the channels and/or chambers (i.e., the interior portion) of the device at the interface of these two components. Bonding of substrates is typically carried out by any of a number of different methods, e.g., thermal bonding, solvent bonding, ultrasonic welding, and the like.

The holes in the top portion of the device are oriented such that they are in communication with at least one of the channels and/or cavities formed in the interior portion of the device from the grooves or indentations in the bottom substrate. In the completed device, these holes function as reservoirs for facilitating fluid or material introduction (e.g., bulk viscosity enhancers, electrolytes, reagents, etc.) into the channels or chambers of the interior portion of the device, as well as providing ports at which electrodes can optionally be placed into contact with fluids within the device, allowing application of electric fields along the channels of the device to control and direct fluid transport within the device. In many embodiments, extensions are provided over these reservoirs to allow for increased fluid volumes, permitting longer running assays, and better controlling fluid flow parameters, e.g., hydrostatic pressures. Examples of methods and apparatuses for providing such extensions are described in U.S. application Ser. No. 09/028,965, filed Feb. 24, 1998, and incorporated herein by reference.

II. Bulk Viscosity Enhancers

The methods and devices of the present invention for regulating spontaneous injection signatures and for controlling electrical resistance generally include the use of bulk viscosity enhancers to vary bulk viscosity levels, e.g., in capillary channels of microfluidic devices. The viscosity or hydrodynamic resistance of a fluid is a measure of the internal friction within the fluid, that is, the resistance of fluid constituents (e.g., polymers, molecules, ions, proteins, polynucleotides, cells, or the like) to movement relative to one another. As mentioned above, bulk viscosity controls convection within a solution, but substantially affects only the diffusion of components having relatively large hydrodynamic radii, such as large polymers. Single atom ions or other comparatively low molecular weight ions diffuse substantially unaffected by bulk viscosity and in general, migrate by Brownian forces relatively unimpeded through the solution. An extensive guide to fluid viscosity and related information can be found in Papanastasiou, T.C. (1999) *Viscous Fluid Flow*, CRC Press, Boca Raton.

A "bulk viscosity enhancer" or "rheological modifer," as used herein, includes molecules capable of increasing the bulk viscosity of a solution. Suitable bulk viscosity enhancers generally include, e.g., any molecule with a hydrodynamic radius that provides high bulk hydrodynamic resistance to a solution, but which permits relatively free diffusion for smaller solution components, such as ions. In other words, bulk viscosity enhancers generally affect the convective motions of different sized molecules to the same extent, but impede the diffusive motions of larger molecules to a greater extent than those of relatively smaller species. Preferred bulk viscosity enhancers are biocompatible and have molecular weights of at least about one kilodalton. For example, bulk viscosity enhancers typically have molecular weights in the range of from about one kilodalton to about 1,000 kilodaltons, generally in the range of from about 5 kilodaltons to about 100 kilodaltons, e.g., about 50 kilodaltons. Other suitable bulk viscosity enhancers are aqueous-based solutions of single polymers, polymer mixtures, copolymers, block copolymers, polymer micellar systems, interpenetration polymer networks, polymer gels, or the like.

Bulk viscosity enhancers include carbohydrates (e.g., polysaccharides) or derivatives thereof. Polysaccharides, or glycans, are polymers of aldehydes or ketones that include two or more hydroxyl groups. These aldehydes and ketones form various monomeric units, such as monosaccharides, disaccharides, and the like. Additionally, polysaccharides include homopolysaccharides or heteropolysaccharides, which can both form straight-chains or branched-chains. Homopolysaccharides are polysaccharides composed of only one type of monomeric unit, whereas heteropolysaccharides include at least two different types of monomeric units. Preferred polysaccharides, or derivatives thereof, include, e.g., polymers or copolymers of glucose (e.g., glycogen, dextran, amylose, amylopectin, cellulose, etc.), fructose, maltose, maltotriose, dextrin, sucrose, maltose, lactose, galactose (e.g., pectins, agars, etc.), and the like. Suitable cellulose derivatives include, e.g., hydroxyethyl cellulose, hydroxypropyl methylcellulose, and the like. Copolymers of sucrose and epichlorohydrin (e.g., FICOLL™) are also preferred.

Other bulk viscosity enhancers suitable for the present invention include, e.g., poly(ethylene glycol), poly(vinyl alcohol), poly(acrylic acids), acrylate copolymers, polyvinyl pyrrolidone (PVP), poly(dimethylacryamides) (PDMA), polyoxyethyleneoxypropyleneglycol block copolymer (e.g., Pluronic™), and the like.

III. Introduction of Bulk Viscosity Enhancers, Surfactants, Electrolytes, and other Reagents into Microfluidic Devices In general, the holes in the top portion of the device are oriented such that they are in communication with at least one of the channels and/or cavities formed in the interior portion of the device from the grooves or indentations in the bottom substrate. The holes optionally function as reservoirs or wells for facilitating fluid or material introduction (e.g., bulk viscosity enhancers, electrolytes, reagents, etc.) into the channels or cavities of the interior portion of the device. Alternatively, these devices are coupled to a sample introduction port, e.g., a pipettor or capillary channel, which serially introduces multiple samples, e.g., from the wells of a microtiter plate.

As noted, sources of bulk viscosity enhancers, surfactants, electrolytes, and other reagents are optionally fluidly coupled to the microchannels in any of a variety of ways. In particular, those systems comprising sources of materials set forth in Knapp et al. "Closed Loop Biochemical Analyzers" (WO 98/45481; PCT/US98/06723) and U.S. Pat. No. 5,942,443 issued Aug. 24, 1999, entitled "High Throughput Screening Assay Systems in Microscale Fluidic Devices" to J. Wallace Parce et al. and, e.g., in Ser. No. 60/128,643 filed Apr. 4, 1999, entitled "Manipulation of Microparticles In Microfluidic Systems," by Mehta et al. are applicable.

In these systems, a "pipettor channel," a "capillary channel," or a "capillary microchannel" (i.e., a channel in which components can be moved from a source to a microscale element such as a second channel or reservoir) is temporarily or permanently coupled to a source of material. The source is optionally internal or external to a microfluidic device comprising the pipettor or capillary channel. Example sources include microwell plates, membranes or other solid substrates comprising lyophilized components, wells or reservoirs in the body of the microscale device itself and others.

For example, the source of bulk viscosity enhancers, surfactants, electrolytes, and other reagents is optionally a microwell plate external to the body structure, having, e.g., at least one well for each of the bulk viscosity enhancers, surfactants, and other reagents. Optionally, bulk viscosity enhancers and surfactants are mixture components in a single well.

As further illustrated in FIG. 1, capillary channel 102 is typically fluidly coupled with a port, such as a well on microtiter plate 106, external to body structure 100. Alternatively, a loading channel is coupled to an electropipettor channel with a port external to the body structure, a pressure-based pipettor channel with a port external to the body structure, a pipettor channel with a port internal to the body structure, an internal channel within the body structure fluidly coupled to a well on the surface of the body structure, an internal channel within the body structure fluidly coupled to a well within the body structure, or the like.

IV. Spontaneous Injection Signature Control

The present invention provides methods of controlling the spontaneous injection signature of, e.g., a microfluidic device that accesses and transports externally stored materials using an external sampling pipettor/interface, such as the device described with respect to FIG. 1. In general, control is typically achieved by varying the buffer properties for introduced reagents or other materials. For example, increasing the viscosity and decreasing the surface tension of a buffer tends to decrease the effects of spontaneous injection. Although the phenomenon of spontaneous injection can be advantageously utilized in particular cases, in others it can have deleterious effects upon an assay. Therefore, methods that afford greater control over the occurrence of spontaneous injection are desirable.

As used herein, the phrase "spontaneous injection" refers to the action of fluid or other material to move into a given passage or conduit under no externally applied forces, e.g., applied pressure differentials, applied electric fields, etc. To illustrate, spontaneous injection typically refers to the action of fluid drop 104 at the tip of capillary channel 102, which is filled with fluid, in moving into the channel as a result of capillary action within the channel, surface tension on the fluid outside the channel, or the like. (FIG. 1). Thus, a fluid or other material that is "spontaneously injected" into a channel, cavity or other conduit, moves into that channel, cavity or other conduit without the assistance of an externally applied motive force. Further, the pressure ($\Delta P$) exerted by spontaneous injection is proportional to the surface tension ($\gamma$) and radius of the drop (R) hanging at the capillary tip according to the expression, as follows:

$$\Delta P = \frac{2\gamma}{R}$$

As mentioned, the characteristics of spontaneous injection can, in certain cases, be exploited, e.g., to provide improved sample accession methods and systems. In particular, spontaneous injection permits a number of useful advantages when sampling large numbers of different materials in microfluidic systems. For example, the rate at which materials are spontaneously injected into a capillary channel is largely dependent upon the geometry of the capillary channel and the nature of the material being sampled, e.g., the type of fluid. Thus, for a given system, spontaneous injection of sample materials is highly reproducible. Further, because spontaneous injection is generally a relatively slow process, one can sample extremely small volumes of materials, depending upon the amount of time over which the material is allowed to inject. Typically, such sampled volumes range from fractions of picoliters to nanoliters.

Additional advantages of spontaneous injection into devices are apparent in electrokinetically controlled systems. In particular, because spontaneous injection does not rely upon electrokinetic introduction of materials into the capillary channel, materials typically less compatible with such electrokinetic systems are optionally used. For example, nonaqueous materials, e.g., pharmaceutical library compounds disposed in nonaqueous solvents such as dimethylsulfoxide (DMSO), dimethylformamide it(DMF), acetone, alcohols and other water soluble organic solvents, nonionic fluids or other materials, can sometimes be less suitable to electrokinetic material transport due to their nonconductive nature or extremely low conductivity. Further, because electric fields are not employed in the initial sampling process, spontaneously injected samples will not have an inherent electrophoretic biasing that is typically associated with electrokinetically sampled materials, where more highly charged components of sample material are enriched for or against, by virtue of the driving electric fields. Additional details regarding spontaneous injection and certain advantages related thereto are provided in, e.g., U.S. Ser. No. 09/416,288 filed Oct. 12, 1999, entitled "External Material Accession Systems and Methods" by Chow, A. W., et al., which is incorporated herein by reference for all purposes.

Despite the advantages of the phenomenon of spontaneous injection in various cases, under other circumstances the effect negatively impacts microfluidic assays and thus is preferably minimized. In a typical pipettor device in a microfluidic high-throughput screening application, substrate and enzyme are brought in from side channels of a microfluidic device. The substrate and enzyme react in the main channel, typically generating a fluorescent product that is detected. During the experiment, a microtiter plate is moved underneath the capillary channel which draws samples from the wells of the microtiter plate into the device. For example, the samples optionally comprise potential inhibitors or other modulators of a fluorogenic enzymatic reaction. With no inhibitor present, an ideal fluorescent signal observed in a screening experiment is flat due to a constant amount of product being generated in the enzymatic reaction. An inhibitor causes a decrease in the amount of fluorescent product generated and thus produces a decrease in the observed signal. Spontaneous injection also leads to decreases in the observed signal.

Spontaneous injection also typically increases the dilution, e.g., of a substrate and an enzyme being introduced from the side channels of the system. The dilution results in a decrease in the observed product signal, which mimics a weakly inhibiting sample being brought onto the chip. When not used as a sampling method, spontaneous injection makes it more difficult to differentiate between weak inhibitors and systematic dips observed in the spectrum. Similar problems exist in other mixing experiments, such as drug screening, nucleic acid sequencing, Western type analyses, and the like. Furthermore, the phenomenon of spontaneous injection can also be a problem in, e.g., capillary electrophoresis applications as it presents a constant volume error in sampling (independent of sampled volume) that typically varies depending upon the geometry of the capillary channel and channel tip.

In microfluidic devices incorporating pipettor channels, if the pressure difference between the tip of the pipettor or capillary channel and intersection point of that channel and, e.g., a main reaction channel is large, then the spontaneous injection signature is typically small. This is optionally achieved by keeping the hydrodynamic resistance high in the capillary channel. As such, the present invention includes methods to control the effects of spontaneous injection by varying buffer conditions. Specifically, the viscosity of a buffer is optionally increased by adding a bulk viscosity enhancer which effects an increase in the hydrodynamic resistance of the capillary channel and reduces the effects of spontaneous injection.

The methods of inducing high bulk hydrodynamic resistance optionally include providing a microscale cavity in the microfluidic device that includes a bulk viscosity enhancer disposed in the cavity. The microscale cavity also optionally includes a capillary microchannel that extends from the microfluidic device. As discussed above, the bulk viscosity enhancer typically includes, e.g., a polymer molecule that has a molecular weight of at least about one kilodalton. Specific examples of suitable bulk viscosity enhancers include biocompatible polymers, such as a polysaccharide (e.g., FICOLL™, dextran, and the like), PEG, PVA, derivatives thereof, or the like. Bulk hydrodynamic resistance in the microscale cavity in the device is optionally regulated by varying or selecting a concentration of the bulk viscosity enhancer disposed in the cavity. The regulated concentration of the bulk viscosity enhancer, in turn, regulates spontaneous injection into the microscale cavity, e.g., during operation of the microfluidic device.

The effects of spontaneous injection are also optionally reduced by adding a surfactant to a buffer. As used herein, a "surfactant" includes amphiphilic materials that spread out along, e.g., a buffer surface, changing the properties of the surface, such as by decreasing the surface tension (i.e., the work required to expand the surface of the liquid by unit area). Suitable surfactants typically include anionic surfactants (e.g., carboxylates, acylated protein hydrosylates, sulfonates, sulfates and sulfated products, phosphate esters, or the like), non-ionic surfactants (e.g., ethoxylates, carboxylic acid esters, carboxylic amides, polyalkylene oxide block copolymers, or the like), cationic surfactants (e.g., amines, 2-alkyl-1-(2-hydroxyethyl)-2-imidazolines, quaternary ammonium salts, or the like), amphoteric surfactants (e.g., imidazolinium derivatives, etc.), or the like.

V. Dispersion Control

Throughput is the rate at which work is performed in a given system. Improvements to the capabilities of analytical instrumentation, such a microfluidic devices, are often made by enhancing device throughput. One way to elevate the throughput of various microfluidic applications is to increase the number of discrete samples or "slugs" of material accommodated per unit length of a given microchannel or other microscale device cavity. A limiting factor such as slug dispersion restricts minimum slug-to-slug spacing in addition to time averaged sample concentrations. As a result, microfluidic devices in which slug dispersion is inhibited in a controllable manner would further improve the throughput and performance of various microfluidic analytical and preparative processes, such as in-line PCRs or the like.

As used herein, the term "dispersion" refers to diffusion and to the convection-induced, longitudinal dispersion of material within a fluid medium due to velocity variations across streamlines, e.g., in pressure driven flow systems, electrokinetically driven flow systems around curves and corners, and electrokinetically driven flow systems having non-uniform buffer ionic concentrations, e.g., plugs of high and low salt solutions within the same channel system. For the purposes of the channel systems of the present invention, dispersion is generally defined as that due to the coupling between flow and molecular diffusion, i.e., Taylor dispersion. In this regime, the time-scale for dispersion due to convective transport is long or comparable to the time scale for molecular diffusion in the direction orthogonal to the flow direction. For discussions on dispersion and Taylor dispersion in particular, see, e.g., Taylor et al., *Proc. Roy. Soc. London* (1953) 219A:186-203, Aris, *Proc. Roy. Soc. London* (1956) A235:67-77, Chatwin et al., *J. Fluid Mech.* (1982) 120:347-358, Doshi et al., *Chem. Eng. Sci.* (1978) 33:795-804, and Gnell et al., *Chem. Eng. Comm.* (1987) 58:231-244, each of which is incorporated herein by reference.

In one aspect, the methods and devices of the present invention utilize bulk viscosity enhancers or rheological modifers and/or temperature to regulate dispersion (e.g., slug dispersion) caused by molecular diffusion or Taylor-Aris dispersion. Bulk viscosity enhancers, such as FICOLL™, dextran, agar, or the like are described in greater detail above. In particular, the invention includes regulating bulk hydrodynamic resistance in a given microscale cavity of a device during run time, e.g., by varying or selecting a concentration of a bulk viscosity enhancer disposed in the cavity and/or by varying or selecting temperatures within the cavity. Optionally, in addition to regulating spontaneous injection into the microscale cavity, e.g., during operation of a device, the regulated bulk hydrodynamic resistance also regulates slug dispersion during fluid flow in the cavity. As described above, decreased dispersion permits reduced slug-to-slug spacing which, in turn, increases throughput. Dispersion control is optionally also effected by varying microscale cavity dimensions and/or fluid residence time in the cavity.

In particular, the effective dispersivity, K, is composed of two components. One component arises from molecular diffusion and the other arises from Taylor-Aris dispersion. The effective dispersivity is $$K = D\left(1 + \frac{f}{210}Pe^2\right). \quad (1)$$

where D is the molecular diffusivity (or diffusion constant), $f$ is a factor that depends on the geometry of the channel, and Pe is the dimensionless Peclet number, which describes the ratio of convective and diffusive transport. Substituting the physical values which make up the Peclet number into equation (1) yields $$K = D\left(1 + \frac{f}{210}\frac{U^2 d^2}{D^2}\right). \quad (2)$$

where U is the average velocity in the channel and d is the channel depth. When designing a microfluidic device, the time the fluid resides in the channel is predetermined. Therefore the average velocity in the channel is U=L/t. Making this substitution into equation (2) yields $$K = D\left(1 + \frac{f}{210}\frac{L^2 d^2}{t^2 D^2}\right) = D + \frac{f}{210}\frac{L^2 d^2}{t^2}\frac{1}{D} = D + \frac{\alpha}{Dt} \quad (3)$$

$$\text{where } \alpha \equiv \frac{f}{210}L^2 d^2.$$

The factor α only depends on the geometry of the channel, and is used for algebraic convenience.

An objective of the present invention is to reduce the total dispersion, which is $$2Kt = 2\left(Dt + \frac{\alpha}{Dt}\right). \quad (4)$$

Total dispersion is minimized when $$(Dt)^* = \sqrt{\alpha} = Ld\sqrt{\frac{f}{210}} \quad (5)$$

Since t is generally fixed, there exists an optimal diffusivity for device operation $$D^* = \frac{Ld}{t}\sqrt{\frac{f}{210}} \quad (6)$$

The molecular diffusivity is dependent on the rheological properties of the surrounding fluid. The Stokes-Einstein relationship states that the diffusivity has the following relationship $$D = \frac{k_B T}{\zeta} = \frac{k_B T}{\mu G}, \quad (7)$$

where $k_B$ is the Boltzmann constant, $\zeta$ is the drag coefficient of the species of interest (e.g., a molecule or particle from a sample), and G is a geometric factor that depends on the shape of the molecule (e.g. G=6πa for spheres with radius a). Equating equations (6) and (7) and solving for viscosity yields $$\mu^* = \frac{k_B T}{G}\frac{t}{Ld}\sqrt{\frac{210}{f}}. \quad (8)$$

Figure 2:
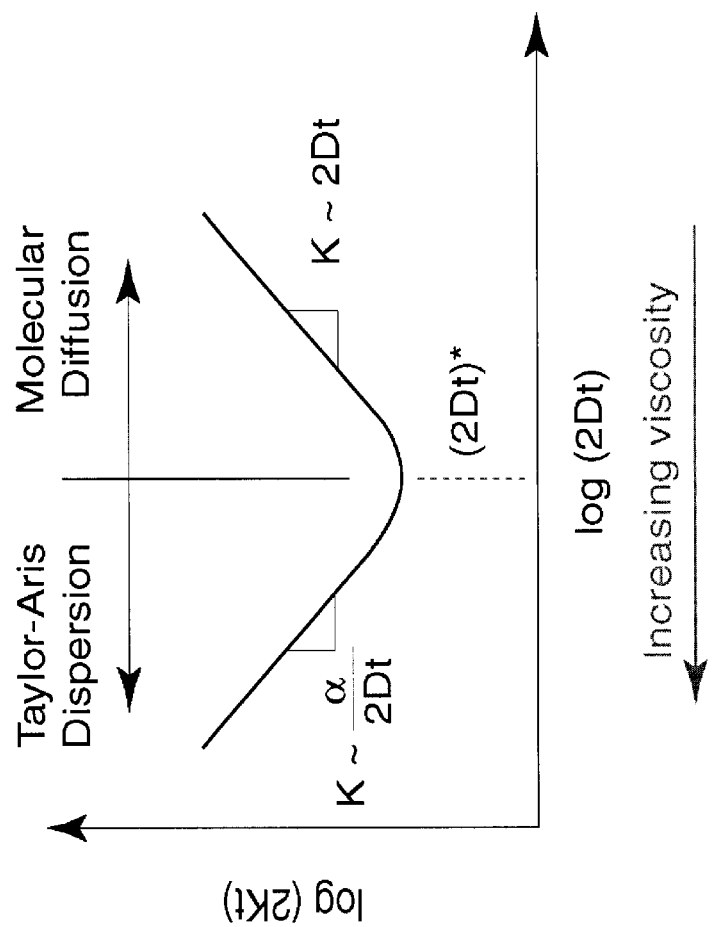
FIG. 2 is a graph that schematically illustrates the dependence of the effective dispersivity on diffusivity.

FIG. 2 is a graph that schematically illustrates the dependence of the effective dispersivity on diffusivity. As shown, when a microfluidic device is operating such that molecular diffusion is reducing throughput, the slug-to-slug spacing is optionally reduced by increasing the viscosity of the transporting fluid, e.g., by increasing the concentration of a bulk viscosity enhancer disposed in the microscale cavity and/or decreasing the temperature of the fluid within the cavity. Conversely, when Taylor-Aris dispersion is limiting throughput, the viscosity is optionally reduced. If the carrier fluid is water, this may be difficult since it is typically challenging to add material to an aqueous phase to reduce the viscosity. However, increased temperature is optionally used to reduce the viscosity. In this case, there is an optimal ratio of $\mu/T$ $$\left(\frac{\mu}{T}\right)^* = \frac{k_B}{G}\frac{t}{Ld}\sqrt{\frac{210}{f}}. \quad (9)$$

VI. Electric Field Regulation

The present invention also relates to the use of high viscosity, high salt buffers loaded into reagent wells of a microfluidic device to induce high hydrodynamic resistance and low electrical resistance. A buffer that includes a bulk viscosity enhancer and an electrolyte is optionally used to achieve these conditions. One significant advantage of this approach is that it generally eliminates using microfluidic devices fabricated with two or more microchannel depths to provide these resistance parameters. Another advantage is that it provides for the control of relative flow rate ratios during device operation (e.g., during the run time of an experiment).

As used herein, an "electrolyte" includes a substance whose aqueous solutions conduct electricity by the movement of ions. Examples of such substances include HCl, HBr, HI, $HNO_3$, $H_2SO_4$, $HClO_4$, or the like. Additionally, electrolytes can include "salts" which include compounds that contain cations other than $H^+$ and anions other than hydroxide ion, $OH^-$, or oxide ion, $O^{2-}$ (e.g., NaCl, KBr, $MgSO_4$, $AgNO_3$, $(NH_4)_2SO_4$, or the like). Some electrolytes are weak acids or bases of salts that also serve as pH buffering species. Suitable salts and other electrolytes are well-known in the art.

Figure 3:
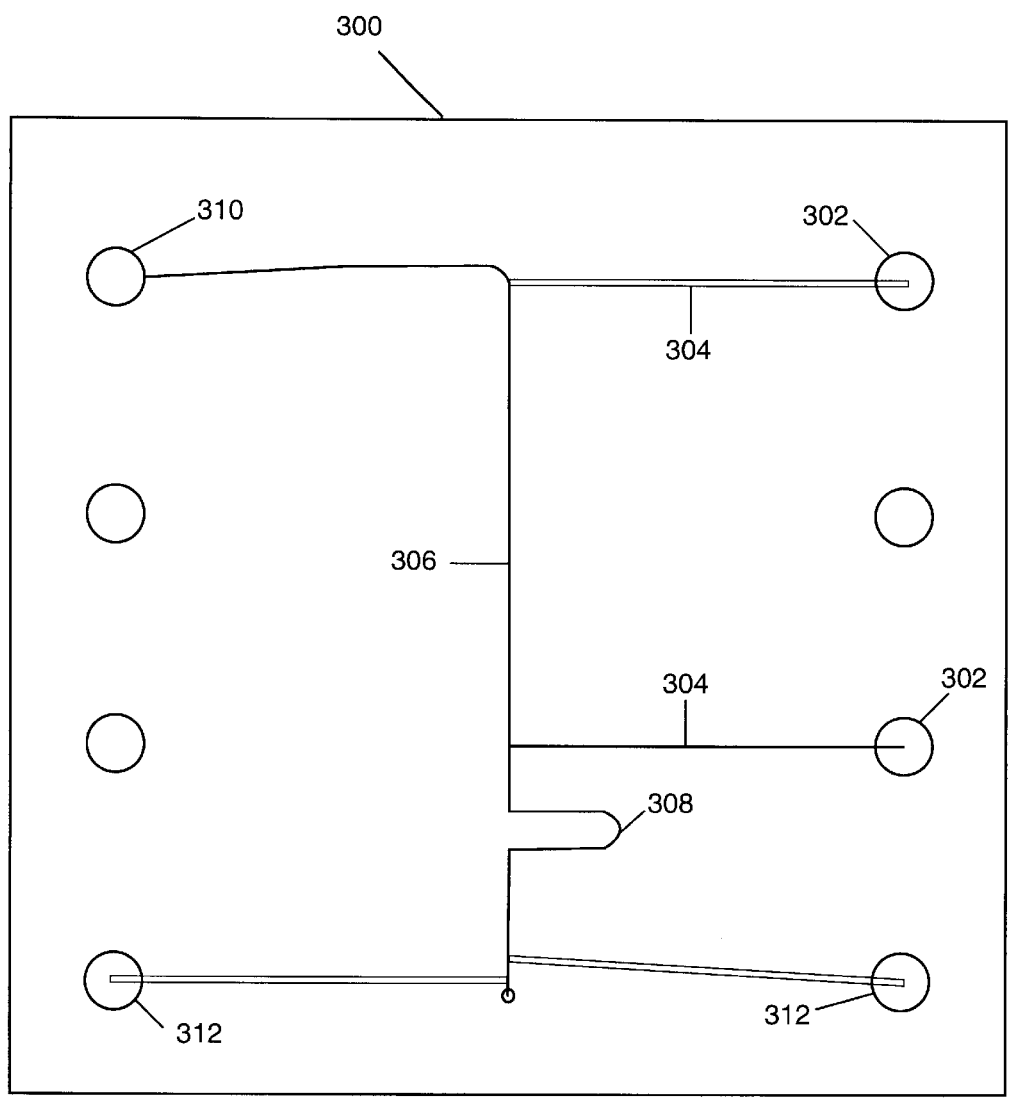
FIG. 3 schematically shows a microfluidic device design that incorporates two microchannel depths.

In some microfluidic applications (e.g., kinase mobility shift assays or the like), microfluidic devices, such as pipettor microfluidic device 300 which includes two microchannel depths and is operated by pressure driven flow supplied by vacuum source 310 are optionally used. (FIG. 3). In operation, side microchannels 304 connecting separation microchannel 306 to reagent wells 302 should be hydrodynamically resistant, but electrically conductive such that flow from reagent wells 302 is small, while a high electrical field is optionally delivered to separation microchannel 306. Assay components such as enzymes, substrates, and the like are optionally introduced into the device from sample wells 312. One way to satisfy both requirements is to make side microchannels 304 shallower and wider than, e.g., separation microchannel 306 and reaction microchannel 308, since hydrodynamic and electrical resistances have different dependencies on microchannel depth. That is, the shallower a given microchannel is the relatively more hydrodynamically resistant and the less electrically resistant it will be. However, making two depth chips adds more complexity and cost to the manufacturing process.

This invention describes devices and methods that provide an alternative to the use of multiple channel depth microfluidic devices and still provide desired hydrodynamic and electrical resistance properties. As mentioned, these methods utilize buffer properties instead of microchannel geometry to meet the specifications. In general, it is well-known that high viscosity fluids increase hydrodynamic resistance in, e.g., pressure driven systems, and that high salt buffers generally increase electrical conductivity. However, in many fluids, increasing viscosity usually decreases electrical conductivity since the increased viscosity generally retards ion mobility. To resolve these conflicting conditions, the present invention uses bulk viscosity enhancers, as discussed above, which optionally include polymers such as a polysaccharide or a derivative thereof (e.g., FICOLL™, dextran, etc.), PEG, PVA, or the like which enhance viscosity, but do not significantly impede ion mobility. Therefore, a tailored buffer such as a high salt buffer with a bulk viscosity enhancer optionally provides the desired resistance parameters in a single buffer using a single channel depth microfluidic device.

Figure 4:
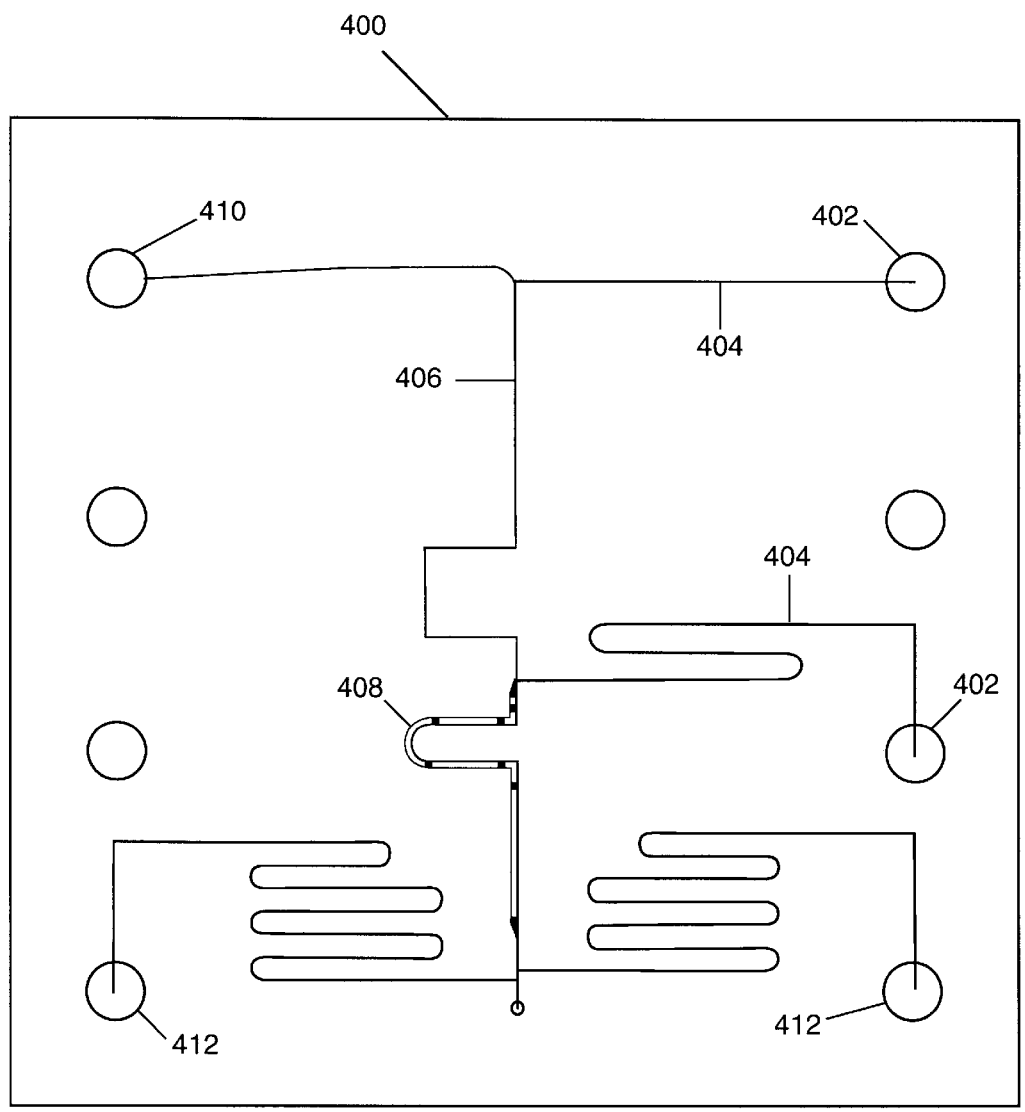
FIG. 4 schematically depicts a microfluidic device design that incorporates a single microchannel depth.

As further shown in FIG. 4, single microchannel depth pipettor microfluidic device 400 is optionally used in conjunction with the methods of the present invention for inducing high bulk hydrodynamic resistance and low electrical resistance to perform the same assays performed in multiple microchannel depth pipettor microfluidic device 300 depicted in FIG. 3. For example, assay components such as enzymes, substrates, or the like are optionally introduced into reaction microchannel 408 and separation microchannel 406 from sample wells 412. Buffers including bulk viscosity enhancers and electrolytes are optionally introduced from reagent wells 402 into side microchannels 404. In so doing, an electric field produced by the electrolyte is optionally delivered to separation microchannel 406. Bulk viscosity enhancers, electrolytes, and other assay components are optionally flowed in the device using, e.g., a fluid pressure force modulator, an electrokinetic force modulator, a capillary force modulator, a fluid wicking element, or the like. Fluid direction components are discussed further, infra. Components are preferably flowed under pressure. For example, pressure is optionally supplied by vacuum source 410.

The bulk hydrodynamic resistance and electrical resistance in the microscale cavities of a microfluidic device are optionally individually or concomitantly regulated by varying or selecting a concentration of at least one bulk viscosity enhancer and/or a concentration of at least one electrolyte disposed in the cavity. Optionally, the bulk hydrodynamic resistance, the electrical resistance, or both, in the microscale cavity is/are regulated, e.g., during operation of the microfluidic device. Additionally, the methods optionally include providing a microchannel disposed in the microfluidic device that intersects and fluidly communicates with the microscale cavity. The regulation of electrical resistance in the microscale cavity typically effects regulation of electrical fields in the intersecting microchannel. Furthermore, electrical current generally affects dilution which adds an additional degree of control. Optionally, the bulk viscosity enhancer and/or electrolyte is/are chosen to modify the electrokinetic velocity in the microscale cavity. For example, polymers such as poly(dimethylacryamide) are known to suppress electroosmotic flow by coating the microchannel walls (i.e., they serve as dynamic coatings). Dynamic coatings are used in various microfluidic applications, including, e.g., DNA sizing. Thus, the methods and devices for achieving high hydrodynamic resistance and low electrical resistance not only lower manufacturing costs, as single channel depth microfluidic devices are optionally used, they also provide another means to control electrical resistance and relative flow rates of reagents within a device, especially during the run time of an experiment. Additionally, an electrolyte is optionally selected to provide more buffering capacities to keep the buffer pH constant during extended screening runs even with electrochemical reactions occurring at the electrodes.

VII. Flow of Reagents in Microscale Systems

The flowing of bulk viscosity enhancers, surfactants, electrolytes, or other reagents along the microchannels of the devices described herein is optionally carried out by a number of mechanisms, including pressure-based flow, electrokinetic flow, or mechanisms that utilize a hybrid of the two. In a preferred aspect, a pressure differential is used to flow the materials along, e.g., a capillary channel, a side channel, an analysis channel, or the like. Application of a pressure differential along the channel is carried out by a number of means. For example, in a simple passive aspect, the reagents are deposited in a reservoir or well at one end of an analysis channel and at a sufficient volume or depth, that the reagent sample creates a hydrostatic pressure differential along the length of the analysis channel, e.g., by virtue of its having greater depth than a reservoir at an opposite terminus of the channel. The hydrostatic pressure then causes the reagents to flow along the length of the channel. Typically, the reservoir volume is quite large in comparison to the volume or flow through rate of the channel, e.g., 10 μl reservoirs, vs. 1000 $\mu m^2$ channel cross-section. As such, over the time course of the assay, the flow rate of the reagents will remain substantially constant, as the volume of the reservoir, and thus, the hydrostatic pressure changes very slowly. Applied pressure is then readily varied to yield different reagent flow rates through the channel. In screening applications, varying the flow rate of the reagents is optionally used to vary the incubation time of the reagents. In particular, by slowing the flow rate along the channel, one can effectively lengthen the amount of time between introduction of reagents and detection of a particular effect. Alternatively, analysis channel lengths, detection points, or reagent introduction points are varied in fabrication of the devices, to vary incubation times.

In many applications, it may be desirable to provide relatively precise control of the flow rate of the electrolytes and/or other reagents, e.g., to precisely control incubation or separation times, etc. As such, in many preferred aspects, flow systems that are more active than hydrostatic pressure driven systems are employed. For example, reagents may be flowed by applying a pressure differential across the length of the analysis channel. For example, a pressure source (positive or negative) is applied at the reagent reservoir at one end of the analysis channel, and the applied pressure forces the reagents through the channel. The pressure source is optionally pneumatic, e.g., a pressurized gas, or a positive displacement mechanism, i.e., a plunger fitted into a reagent reservoir, for forcing the reagents through the analysis channel. Alternatively, a vacuum source is applied to a reservoir at the opposite end of the channel to draw the reagents through the channel. Pressure or vacuum sources may be supplied external to the device or system, e.g., external vacuum or pressure pumps sealably fitted to the inlet or outlet of the analysis channel, or they may be internal to the device, e.g., microfabricated pumps integrated into the device and operably linked to the analysis channel. Examples of microfabricated pumps have been widely described in the art. See, e.g., published International Application No. WO 97/02357.

In alternate aspects, other flow systems are employed in transporting reagents through the analysis channel. One example of such alternate methods employs electrokinetic forces to transport the reagents. Electrokinetic transport systems typically utilize electric fields applied along the length of channels that have a surface potential or charge associated therewith. When fluid is introduced into the channel, the charged groups on the inner surface of the channel ionize, creating locally concentrated levels of ions near the fluid surface interface. Under an electric field, this charged sheath migrates toward the cathode or anode (depending upon whether the sheath comprises positive or negative ions) and pulls the encompassed fluid along with it, resulting in bulk fluid flow. This flow of fluid is generally termed electroosmotic flow. Where the fluid includes reagents, the reagents are also pulled along. A more detailed description of controlled electrokinetic material transport systems in microfluidic systems is described in published International Patent Application No. WO 96/04547, which is incorporated herein by reference.

Hydrostatic, wicking and capillary forces are also optionally used to provide for fluid flow. See, e.g., "Method and Apparatus for Continuous liquid Flow in Microscale Channels Using Pressure Injection, Wicking and Electrokinetic Injection," by Alajoki et al., U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure.

In alternative aspects, flow of reagents is driven by centrifugal forces. In particular, the analysis channel is optionally disposed in a substrate that has the conformation of a rotor, with the analysis channel extending radially outward from the center of the rotor. The reagents are deposited in a reservoir that is located at the interior portion of the rotor and is fluidly connected to the channel. During rotation of the rotor, the centripetal force on the reagents forces the reagents through the analysis channel, outward toward the edge of the rotor. Multiple analysis channels are optionally provided in the rotor to perform multiple different analyses. Detection of a detectable signal produced by the reagents is then carried out by placing a detector under the spinning rotor and detecting the signal as the analysis channel passes over the detector. Examples of rotor systems have been previously described for performing a number of different assay types. See, e.g., Published International Application No. WO 95/02189. Test compound reservoirs are optionally provided in the rotor, in fluid communication with the analysis channel, such that the rotation of the rotor also forces the test compounds into the analysis channel.

For purposes of illustration the discussion has focused on a single channel and accessing capillary, however, it will be readily appreciated that these aspects may be provided as multiple parallel analysis channels and accessing capillaries, in order to substantially increase the throughput of the system. Specifically, single body structures may be provided with multiple parallel analysis channels coupled to multiple sample accessing capillaries that are positioned to sample multiple samples at a time from sample libraries, e.g., multiwell plates. As such, these capillaries are generally spaced at regular distances that correspond with the spacing of wells in multiwell plates, e.g., 9 mm centers for 96 well plates, 4.5 mm for 384 well plates, and 2.25 mm for 1536 well plates.

VIII. Integrated Systems

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., particle separation, extraction, purification, amplification, cellular activation, labeling reactions, dilution, aliquotting, and the like. Similarly, downstream operations may include similar operations, including, e.g., separation of sample components, labeling of components, assays and detection operations, electrokinetic or pressure-based injection of components into contact with particle sets, or materials released from particle sets, or the like.

Assay and detection operations include, without limitation, cell fluorescence assays, cell activity assays, probe interrogation assays, e.g., nucleic acid hybridization assays utilizing individual probes, free or tethered within the channels or chambers of the device and/or probe arrays having large numbers of different, discretely positioned probes, receptor/ligand assays, immunoassays, and the like. Any of these elements are optionally fixed to array members, or fixed, e.g., to channel walls, or the like.

In general, the devices or systems of the invention optionally include an integrated system that incorporates a computer or a computer readable medium that generally includes an instruction set for varying or selecting a concentration of, e.g., a bulk viscosity enhancer and/or surfactant disposed in, e.g., a capillary microchannel that extends from the microfluidic device. The varied or selected bulk viscosity enhancer and/or surfactant concentration, in this manner regulates bulk hydrodynamic resistance within the microscale cavity which, in turn, regulates spontaneous injection into the microscale cavity. Spontaneous injection is optionally regulated during operation of the device. Optionally, the computer or computer readable medium also includes an instruction set for varying or selecting a temperature within the microscale cavity, e.g., to regulate slug dispersion according to the methods described herein.

The invention also optionally includes a device or system that includes a body structure having one or more microchannel fabricated in the structure that optionally includes a mixture of a bulk viscosity enhancer and an electrolyte. Additionally, this device or system typically includes an integrated system that also includes a computer or a computer readable medium that includes an instruction set. The instruction set optionally varies or selects concentrations of the bulk viscosity enhancer and/or the electrolyte disposed in a microchannel to regulate bulk hydrodynamic resistance and electrical resistance within the device. In another aspect, the regulated bulk hydrodynamic resistance within the microscale cavity regulates dispersion (e.g., slug dispersion) during fluid flow in the microscale cavity.

Instrumentation

In the present invention, the materials are optionally monitored and/or detected so that an activity can be determined. The systems described herein generally include microfluidic devices, as described above, in conjunction with additional instrumentation for controlling spontaneous injection, electric fields, fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Controllers

A variety of controlling instrumentation is optionally utilized in conjunction with the microfluidic devices described above, for controlling the transport, concentration, and direction of fluids (e.g., to regulate the effects of spontaneous injection and/or electrical resistance) and/or materials within the devices of the present invention, e.g., by pressure-based or electrokinetic control.

As described above, in many cases, fluid transport, concentration, and direction (e.g., of bulk viscosity enhancers, electrolytes, reagents, or the like) are controlled in whole or in part, using pressure based flow systems that incorporate external or internal pressure sources to drive fluid flow. Internal sources include microfabricated pumps, e.g., diaphragm pumps, thermal pumps, and the like that have been described in the art. See, e.g., U.S. Pat. Nos. 5,271,724, 5,277,556, and 5,375,979 and Published PCT Application Nos. WO 94/05414 and WO 97/02357. As also noted above, the systems described herein can also utilize electrokinetic material direction and transport systems. Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. See, e.g., FIG. 4. Example systems are also described in U.S. Ser. No. 09/238,467 filed Jan. 28, 1999.

Typically, the controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also used to provide for electrokinetic injection or withdrawal of material downstream of the region of interest to control an upstream flow rate. The same instrumentation and techniques described above are also utilized to inject a fluid into a downstream port to function as a flow control element.

Detector

The devices herein optionally include signal detectors, e.g., which detect concentration, fluorescence, phosphorescence, radioactivity, pH, charge, absorbance, refractive index, luminescence, temperature, magnetism, mass, or the like. The detector(s) optionally monitors one or a plurality of signals from upstream and/or downstream of an assay mixing point in which, e.g., a ligand and an enzyme are mixed. For example, the detector optionally monitors a plurality of optical signals which correspond in position to "real time" assay results.

Example detectors or sensors include photomultiplier tubes, CCD arrays, optical sensors, temperature sensors, pressure sensors, pH sensors, conductivity sensors, mass sensors, scanning detectors, or the like. Cells or other components which emit a detectable signal are optionally flowed past the detector, or, alternatively, the detector can move relative to the array to determine the position of an assay component (or, the detector can simultaneously monitor a number of spatial positions corresponding to channel regions, e.g., as in a CCD array). Each of these types of sensors is optionally readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. The detector optionally includes or is operably linked to a computer, e.g., which has software for converting detector signal information into assay result information (e.g., kinetic data of modulator activity), or the like. A microfluidic system optionally employs multiple different detection systems for monitoring the output of the system. Detection systems of the present invention are used to detect and monitor the materials in a particular channel region (or other reaction detection region).

The detector optionally exists as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

Computer

As noted above, either or both of the controller system and/or the detection system is/are optionally coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation, such as varying or selecting bulk viscosity enhancer and/or electrolyte concentrations. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring of materials, such as bulk viscosity enhancers, surfactants, and/or electrolyte concentrations in the channels. Additionally, the software is optionally used to control pressure or electrokinetic modulated injection or withdrawal of material. The injection or withdrawal is used to modulate the effects of spontaneous injection, electrical resistance, flow rate, and the like as described above.

Example Integrated System

Figure 5:
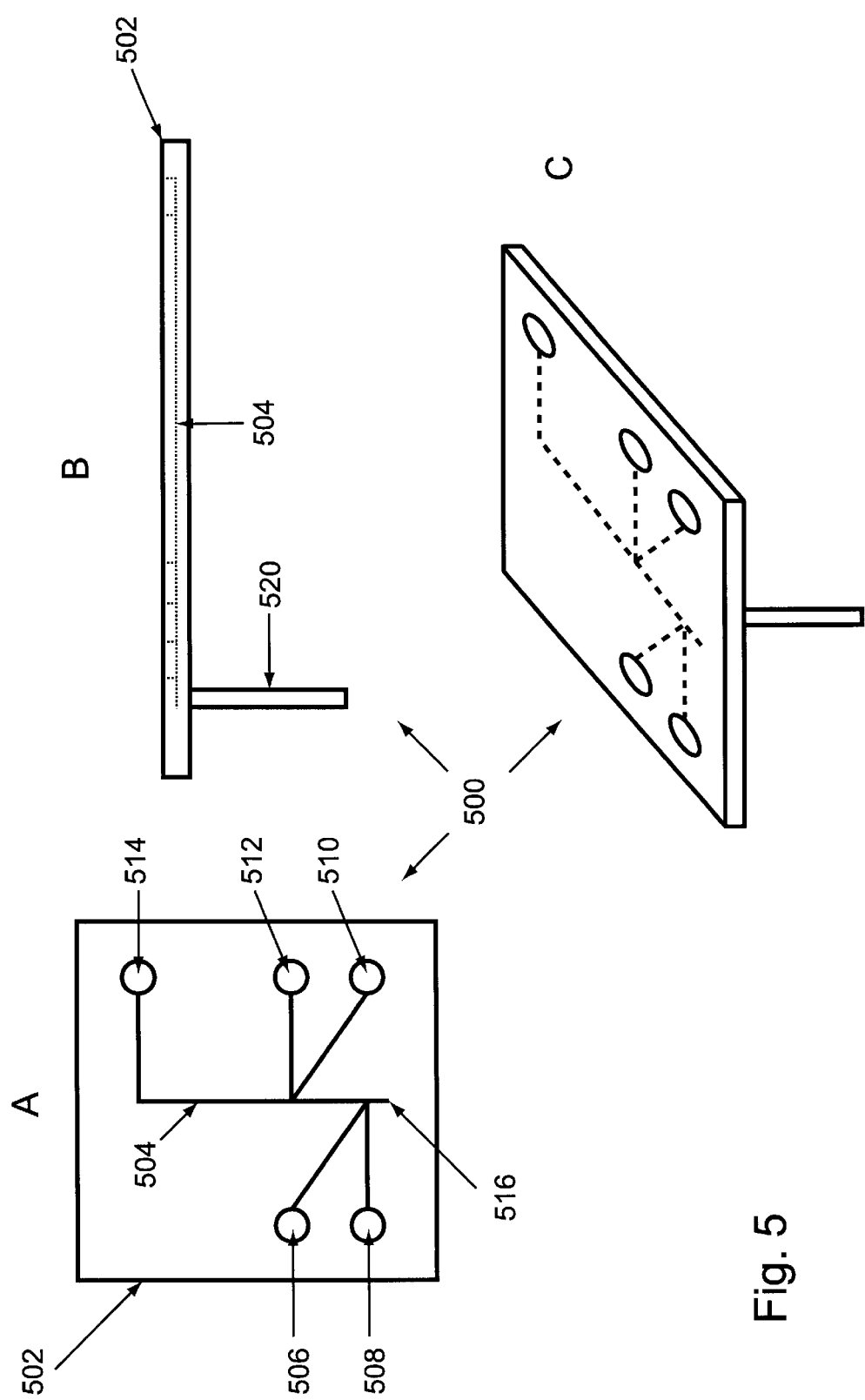
FIGS. 5A–5C schematically show a microfluidic device that includes a capillary element from various viewpoints.
Figure 6:
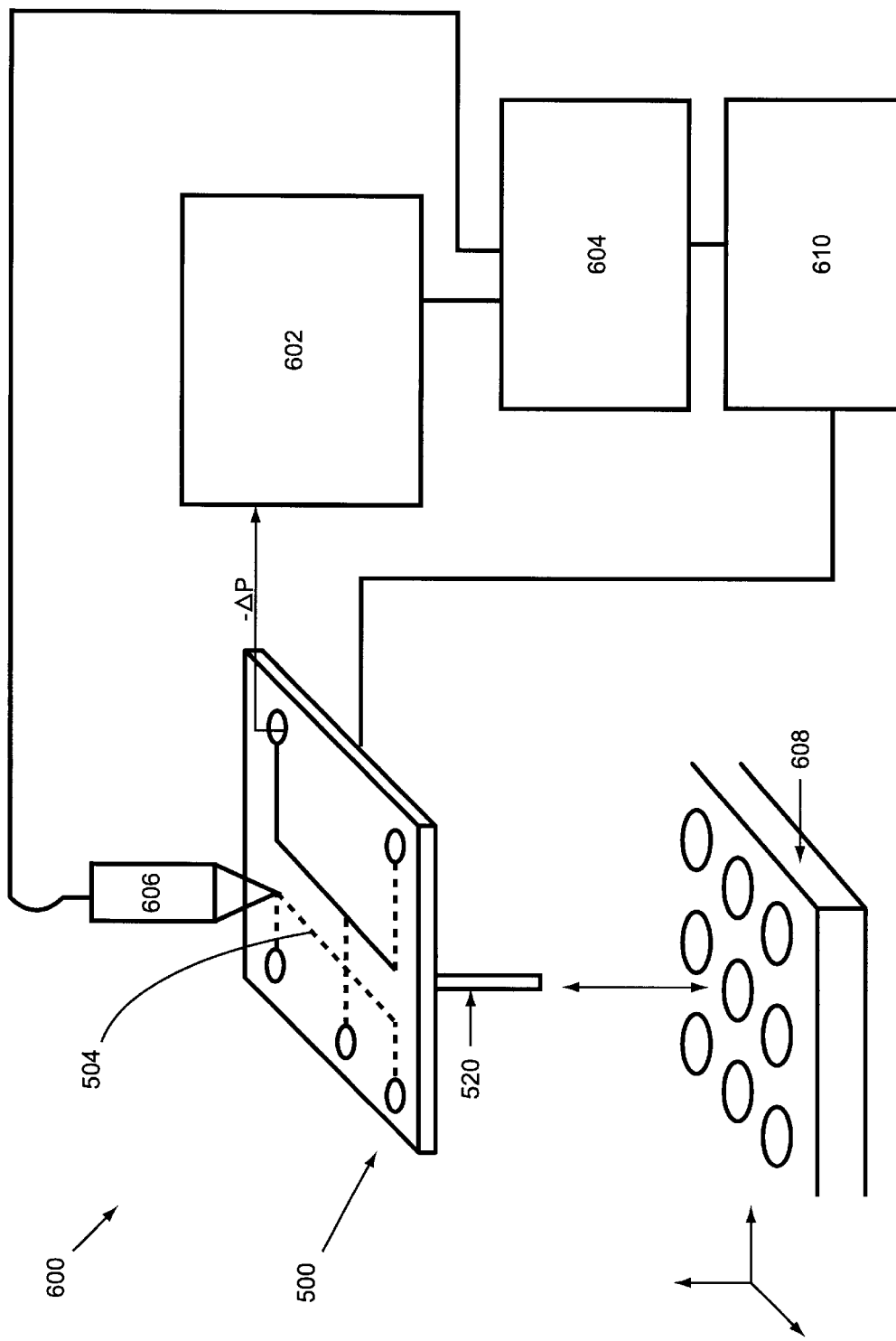
FIG. 6 schematically illustrates an integrated system that includes the microfluidic device of FIGS. 5A–5C.

FIG. 5, Panels A, B, and C and FIG. 6 provide additional details regarding example integrated systems that are optionally used to practice the methods herein. As shown, body structure 502 of microfluidic device 500 has main microchannel 504 disposed therein. Bulk viscosity enhancers, electrolytes, and/or other materials are optionally flowed from pipettor or capillary element 520 towards reservoir 514, e.g., by applying a vacuum at reservoir 514 (or another point in the system) and/or by applying appropriate voltage gradients, e.g., to regulate spontaneous injection signatures and/or electric fields, as described herein. Alternatively, a vacuum is applied at reservoirs 508, 512 or through pipettor or capillary element 520. Additional materials including bulk viscosity enhancers and/or electrolytes are optionally flowed from wells 508 or 512 and into main microchannel 504, e.g., to regulate slug dispersion and/or electric fields, etc. according to the methods of the invention. Flow from these wells is optionally performed by modulating fluid pressure, or by electrokinetic approaches as described (or both). As fluid is added to main microchannel 504, e.g., from reservoir 508, the flow rate increases. The flow rate is optionally reduced by flowing a portion of the fluid from main microchannel 504 into flow reduction microchannel 506 or 510. The arrangement of channels depicted in FIG. 5 is only one possible arrangement out of many which are appropriate and available for use in the present invention. Additional alternatives can be devised, e.g., by combining the microfluidic elements described herein with other microfluidic device components described in the patents and applications referenced herein.

Samples or other materials are optionally flowed from the enumerated wells or from a source external to the body structure. As depicted, the integrated system optionally includes pipettor or capillary element 520, e.g., protruding from body 502, for accessing a source of materials external to the microfluidic system. Typically, the external source is a microtiter dish, a substrate, a membrane, or other convenient storage medium. For example, as depicted in FIG. 6, pipettor or capillary element 520 can access microwell plate 608, which includes sample materials, buffers, substrate solutions, enzyme solutions, or the like, in the wells of the plate.

Detector 606 is in sensory communication with main microchannel 504, detecting signals resulting, e.g., from labeled materials flowing through the detection region. Detector 606 is optionally coupled to any of the channels or regions of the device where detection is desired. Detector 606 is operably linked to computer 604, which digitizes, stores, and manipulates signal information detected by detector 606, e.g., using any instruction set, e.g., for determining concentration, molecular weight or identity, or the like.

Fluid direction system 602 controls pressure, voltage, or both, e.g., at the wells of the system or through the channels or other cavities of the system, or at vacuum couplings fluidly coupled to main microchannel 504 or other channels described above. Optionally, as depicted, computer 604 controls fluid direction system 602. In one set of embodiments, computer 604 uses signal information to select further parameters for the microfluidic system. For example, upon detecting the presence of a component of interest (e.g., following separation) in a sample from microwell plate 608, the computer optionally directs addition of a potential modulator of the component of interest into the system. In certain embodiments, controller 610 dispenses aliquots of selected material into, e.g., main microchannel 504. In these embodiments, controller 610 is also typically operably connected to computer 604, which directs controller 610 function.

Although not shown, a microfluidic device handling system is also included in the integrated systems of the present invention. Microfluidic device handling systems generally control, e.g., the X-Y-Z translation of microfluidic device 500 relative to microwell plate 608, of microwell plate 608 relative to microfluidic device 500, or of other system components, under the direction of computer 604, e.g., according to appropriate program instructions, to which device handling systems are typically operably connected.

IX. Kits

Generally, the microfluidic devices described herein are optionally packaged to include reagents for performing the device's preferred function. For example, the kits can include any of microfluidic devices described along with assay components, bulk viscosity enhancers, electrolytes, reagents, sample materials, proteins, antibodies, enzymes, substrates, control materials, spacers, buffers, immiscible fluids, or the like. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one embodiment, the device itself comprises a pipettor element, such as an electropipettor for introducing material into channels and chambers within the device). In the former case, such kits typically include a microfluidic device with necessary reagents predisposed in the channels/ chambers of the device.

Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like. Kits also optionally include packaging materials or containers for holding microfluidic device, system or reagent elements.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were individually so denoted.

What is claimed is:

1. A method of inducing high bulk hydrodynamic resistance in a microfluidic device, the method comprising:
    providing at least one microscale cavity in the microfluidic device;
    introducing a fluid into the microscale cavity, the fluid comprising an analyte and at least one bulk viscosity enhancer, wherein the at least one bulk viscosity enhancer effects an increase in bulk hydrodynamic resistance of the fluid within the at least one microscale cavity, thereby inducing high bulk hydrodynamic resistance in the microfluidic device.

2. The method of claim 1, wherein the at least one microscale cavity is at least one capillary microchannel.

3. The method of claim 1, wherein the at least one bulk viscosity enhancer is flowed in the microfluidic device using one or more fluid direction components comprising one or more of: a fluid pressure force modulator, an electrokinetic force modulator, a capillary force modulator, or a fluid wicking element.

4. The method of claim 1, wherein the bulk hydrodynamic resistance in the at least one microscale cavity in the microfluidic device is regulated by varying or selecting a concentration of the at least one bulk viscosity enhancer in the fluid disposed therein, by varying or selecting a temperature within the at least one microscale cavity, or both.

5. The method of claim 4, wherein the regulated bulk hydrodynamic resistance thereby regulates dispersion during fluid flow in the at least one microscale cavity.

6. The method of claim 4, wherein the regulated bulk hydrodynamic resistance thereby regulates spontaneous injection into the at least one microscale cavity.

7. The method of claim 6, further comprising regulating the spontaneous injection by varying or selecting a concentration of at least one surfactant in the fluid disposed in the at least one microscale cavity.

8. The method of claim 6, comprising regulating the spontaneous injection during operation of the microfluidic device.

9. The method of claim 6, wherein the at least one microscale cavity is at least one capillary microchannel.

10. The method of claim 9, wherein the at least one capillary microchannel extends from the microfluidic device.

11. The method of claim 1, further comprising inducing low electrical resistance in the microfluidic device, the method comprising:
    providing at least one electrolyte in the fluid disposed in the at least one microscale cavity, wherein diffusive mobility of the at least one electrolyte is substantially unaffected by the increase in bulk hydrodynamic resistance within the at least one microscale cavity, thereby inducing low electrical resistance in the microfluidic device.

12. The method of claim 11, wherein the at least one microscale cavity is a microchannel.

13. The method of claim 11, wherein the at least one bulk viscosity enhancer and the at least one electrolyte are flowed in the microfluidic device using one or more fluid direction components comprising one or more of: a fluid pressure force modulator, an electrokinetic force modulator, a capillary force modulator, or a fluid wicking element.

14. The method of claim 11, wherein the at least one electrolyte comprises at least one salt or at least one buffering ionic species.

15. The method of claim 1 or 11, wherein the at least one bulk viscosity enhancer comprises a biocompatible polymer.

16. The method of claim 1 or 11, wherein the at least one bulk viscosity enhancer comprises a molecular weight of at least about one kilodalton.

17. The method of claims 1 or 11, wherein the at least one bulk viscosity enhancer comprises one or more of: a single polymer, a mixture of polymers, a copolymer, a block copolymer, a polymer micellar system, an interpenetrating polymer network, a polymer gel, a polysaccharide, a poly (ethylene glycol), a poly(vinyl alcohol), a poly (dimethylacryamide), or a derivative thereof.

18. The method of claim 17, wherein the at least one bulk viscosity enhancer is disposed in an aqueous solution.

19. The method of claim 11, wherein the bulk hydrodynamic resistance of the fluid in the at least one microscale cavity in the microfluidic device is regulated by varying or selecting a concentration of the at least one bulk viscosity enhancer in the fluid disposed therein; or,
    wherein the electrical resistance in the at least one microscale cavity in the microfluidic device is regulated by varying or selecting a concentration of the at least one electrolyte in the fluid disposed therein; or,
    wherein the bulk hydrodynamic resistance of the fluid and the electrical resistance in the at least one microscale cavity in the microfluidic device are regulated by concomitantly varying or selecting a concentration of the at least one bulk viscosity enhancer and a concentration of the at least one electrolyte disposed in the fluid therein.

20. The method of claim 19, comprising providing at least one microchannel disposed in the microfluidic device, the at least one microchannel intersecting and fluidly communicating with the at least one microscale cavity, whereby regulating the electrical resistance in the at least one microscale cavity thereby regulates electrical resistance in the at least one microchannel.

21. The method of claim 20, comprising regulating the bulk hydrodynamic resistance, the electrical resistance, or both, of a fluid in the at least one microscale cavity during operation of the microfluidic device.

22. A device or system, comprising:
a body structure comprising at least one microscale cavity extending therefrom; and,
the at least one microscale cavity containing a fluid comprising an analyte and at least one bulk viscosity enhancer.

23. The device or system of claim 22, wherein the at least one microscale cavity is at least one capillary microchannel.

24. The device or system of claim 22, wherein the at least one bulk viscosity enhancer is flowed in the device or system using one or more fluid direction components comprising one or more of: a fluid pressure force modulator, an electrokinetic force modulator, a capillary force modulator, or a fluid wicking element.

25. The device or system of claim 22, wherein the at least one bulk viscosity enhancer comprises a biocompatible polymer.

26. The device or system of claim 22, wherein the at least one bulk viscosity enhancer comprises a molecular weight of at least about one kilodalton.

27. The device or system of claim 22, wherein the at least one bulk viscosity enhancer comprises one or more of: a single polymer, a mixture of polymers, a copolymer, a block copolymer, a polymer micellar system, an interpenetrating polymer network, a polymer gel, a polysaccharide, a poly(ethylene glycol), a poly(vinyl alcohol), a poly(dimethylacryamide), or a derivative thereof.

28. The device or system of claim 27, wherein the at least one bulk viscosity enhancer is disposed in an aqueous solution.

29. The device or system of claim 22, further comprising an integrated system comprising a computer or a computer readable medium comprising an instruction set for varying or selecting a concentration of the at least one bulk viscosity enhancer in the fluid disposed in the at least one microscale cavity, for varying or selecting a temperature within the at least one microscale cavity, or both, thereby regulating bulk hydrodynamic resistance of the fluid within the at least one microscale cavity.

30. The device or system of claim 29, wherein the regulated bulk hydrodynamic resistance of the fluid within the at least one microscale cavity thereby regulates dispersion during fluid flow in the at least one microscale cavity.

31. The device or system of claim 29, wherein the regulated bulk hydrodynamic resistance of the fluid within the at least one microscale cavity thereby regulates spontaneous injection into the at least one microscale cavity.

32. The device or system of claim 31, further comprising regulating the spontaneous injection by varying or selecting a concentration of at least one surfactant disposed in the at least one microscale cavity.

33. The device or system of claim 31, comprising regulating the spontaneous injection during operation of the device.

34. The device or system of claim 31, wherein the at least one microscale cavity is at least one capillary microchannel.

35. The device or system of claim 34, wherein the at least one capillary microchannel extends from the microfluidic device.

36. A device or system, comprising:
a body structure having at least one microscale cavity fabricated therein; and,
the at least one microscale cavity containing a fluid comprising an analyte, at least one bulk viscosity enhancer, and at least one electrolyte.

37. The device or system of claim 36, wherein the at least one microscale cavity is a microchannel.

38. The device or system of claim 36, wherein the at least one bulk viscosity enhancer and the at least one electrolyte are flowed in the device or system using one or more fluid direction components comprising one or more of: a fluid pressure force modulator, an electrokinetic force modulator, a capillary force modulator, or a fluid wicking element.

39. The device or system of claim 36, wherein the at least one electrolyte is at least one salt or at least one buffering ionic species.

40. The device or system of claim 36, wherein the at least one bulk viscosity enhancer comprises a biocompatible polymer.

41. The device or system of claim 36, wherein the at least one bulk viscosity enhancer comprises a molecular weight of at least about one kilodalton.

42. The device or system of claim 36, wherein the at least one bulk viscosity enhancer comprises one or more of: a single polymer, a mixture of polymers, a copolymer, a block copolymer, a polymer micellar system, an interpenetrating polymer network, a polymer gel, a polysaccharide, a poly(ethylene glycol), a poly(vinyl alcohol), a poly(dimethylacryamide), or a derivative thereof.

43. The device or system of claim 42, wherein the at least one bulk viscosity enhancer is disposed in an aqueous solution.

44. The device or system of claim 36, further comprising an integrated system comprising a computer or a computer readable medium comprising an instruction set for varying or selecting concentrations of the at least one bulk viscosity enhancer and the at least one electrolyte in the fluid disposed in the at least one microscale cavity, thereby regulating bulk hydrodynamic resistance and electrical resistance within the at least one microscale cavity.

45. The device or system of claim 44, further comprising at least one microchannel fabricated in the body structure, wherein the at least one microchannel intersects and fluidly communicates with the at least one microscale cavity, whereby regulating the electrical resistance within the at least one microscale cavity thereby regulates electrical resistance in the at least one microchannel.

46. The device or system of claim 45, comprising regulating the bulk hydrodynamic resistance, the electrical resistance, or both, within the at least one microscale cavity during operation of the device.

* * * * *

UNITED STATES PATENT AND TRADEMARK OFFICE
CERTIFICATE OF CORRECTION

PATENT NO.     : 6,669,831 B2
DATED          : December 30, 2003
INVENTOR(S)    : Chow et al.

It is certified that error appears in the above-identified patent and that said Letters Patent is hereby corrected as shown below:

Column 24,
Line 40, please delete "dimethylacryamide" and insert -- dimethylacrylamide --.

Column 25,
Line 29, please delete "dimethylacryamide" and insert -- dimethylacrylamide --.

Column 26,
Line 34, please delete "dimethylacryamide" and insert -- dimethylacrylamide --.
Line 56, before "within" please insert -- of the fluid --.

Signed and Sealed this

Sixteenth Day of March, 2004

JON W. DUDAS
*Acting Director of the United States Patent and Trademark Office*